United States Patent [19]

Fouletier et al.

[11] Patent Number: 4,526,674
[45] Date of Patent: Jul. 2, 1985

[54] OXYGEN GAUGE THE WORKING ELECTRODE OF WHICH IS COMPOSED OF A MACROCYCLIC PYROLIC COMPOUND

[75] Inventors: Mireille Fouletier; Elisabeth Siebert, both of Grenoble; Jacques Le Moigne, Strasbourg, all of France

[73] Assignee: Societe Nationale Elf Aquitaine, Courbevoie, France

[21] Appl. No.: 636,546

[22] Filed: Aug. 1, 1984

[30] Foreign Application Priority Data

Aug. 3, 1983 [FR] France .................... 83 12799

[51] Int. Cl.³ ............................ G01N 27/58
[52] U.S. Cl. ........................................ 204/426
[58] Field of Search .............. 204/421, 424, 425, 426, 204/427, 428, 429, 15

[56] References Cited

U.S. PATENT DOCUMENTS

Re. 28,792 4/1976 Ruka et al. .................. 204/1 T

OTHER PUBLICATIONS

S. Asavapiriyanont et al., J. Electroanal. Chem., 177, pp. 229–251, (1984).

Primary Examiner—G. L. Kaplan
Attorney, Agent, or Firm—Weiser & Stapler

[57] ABSTRACT

Oxygen gauges in which the working electrode is composed of a macrocyclic pyrolic compound.

These gauges are intended to be used for the measurement of oxygen concentration in a gaseous medium.

Application for the measurement of oxygen partial pressure at low temperatures.

6 Claims, 4 Drawing Figures

OXYGEN GAUGE THE WORKING ELECTRODE OF WHICH IS COMPOSED OF A MACROCYCLIC PYROLIC COMPOUND

BACKGROUND OF THE INVENTION

Field of the Invention

The present invention concerns improvements to oxygen gauges. The principle of oxygen gauges, which is well known to the man skilled in the art, is essentially based on the use of a reference electrode, an ion conductive electrolyte and a working electrode sensitive to the oxygen partial pressure.

The best known gauges or sensors use zirconium dioxide ($ZrO_2$) doped with yttrium oxide ($Y_2O_3$) or calcium oxide (CaO). The operating temperature of the cell is more than 400° C. due to the low conductivity at low temperature of this solid solution. The utilisation of other solid solutions based on cerium oxide ($CeO_2$) or bismuth oxide ($Bi_2O_3$), has been envisaged. However, at a temperature lower than 400° C., the response time of the sensor (i.e. the time necessary for the e.m.f. of the sensor to become, after modification of the oxygen pressure of the gas, equals approximately 50% ($t_{50}$) or 90% ($t_{90}$) of the theoretical e.m.f.) becomes very high. On the other hand in the presence of a reducing gas, the electronic conductivity of these oxides is important and therefore the use of such electrolytes can only be envisaged for the measure of oxygen contents higher than 1%.

To remedy these difficulties a solid electrolyte has been used, the conductivity of which is mainly due to ions other than the oxide ions. Anion conducting solid electrolytes (chlorides, fluorides) synthesized in the past few years show sufficient conductivity at room temperature. The use of a lead fluostannate $PbSnF_4$ has been proposed in French published Patent Application No. 2 486 244. Another French Patent Application, FP-ANo 82 13473 the title of which is "Electrochemical device for the measurement of partial pressure of oxygen in a gaseous or liquid atmosphere", proposes to dissolve in the lead fluostannate, peroxide ions for example 0.5% of barium peroxide ($BaO_2$). Response time of the sensor has in this way been considerably reduced. However, operating temperature of the sensor, cannot be lower than 150° C. due to the prohibitive increase in the response time of the sensor.

The object of the present invention is to realize oxygen gauges able to be used at temperatures below 150° C., specially below 100° C. and leading to excellent response times.

The present invention thus proposes an oxygen gauge of the type mentioned herein above in which the working electrode is constituted, at least partly, by a macrocyclic tetrapyrolic material.

The macrocyclic material can be chosen from the porphyrines shown in formula I:

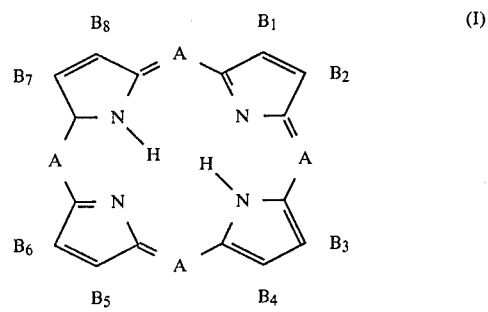

In this formula:
the groups $B_1$ to $B_8$, which can be identical or different, each represent H or a methyl or ethyl radical.
A represents either nitrogen in which case tetra-azoporphyrines are involved or represent C-H or a C-phenyl group.

Specially adapted tetra-azoporphyrines for the carrying out of the present invention are represented by formula II:

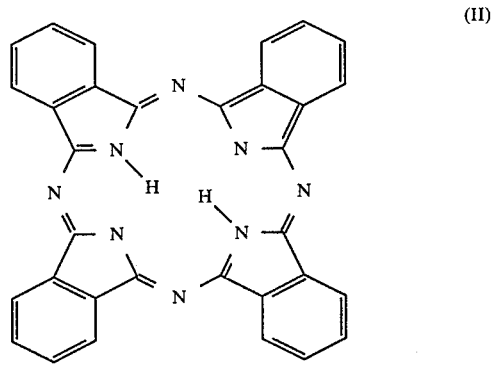

These derivatives correspond to the derivatives of formula I wherein the position of two adjacent radicals $B_1$ to $B_8$ are occupied by benzenic cycles condensed on the pyrolic cycle.

Among these derivatives, particularly the ones obtained by substituting the protons by a halogen (chlorine or fluorine) or by condensation of benzenic cycles (naphthophthalocyanine) will be used.

Preferably the macrocyclic material is a metallic complex, chosen among complexes of iron, nickel or cobalt.

The advantage of the working electrode according to the present invention is due to the fact that the macrocyclic tetra pyrolic materials already show at room temperature excellent catalyzing properties with respect to oxygen reduction;

In the case of metallic complexes, the electronic structure of the central atom is more particularly an important parameter for the catalyzing properties.

According to another embodiment, the electrolyte is a lead fluostannate doped with barium peroxide in which the peroxide is dissolved at 0.5%. This type of electrolyte is described in French patent application No. 82 13473.

According to another characteristic, the material of the reference electrode is a mixture of tin and of tin fluoride in contact with the electrolyte and isolated from atmosphere by an impervious resin.

According to the invention, the electrode material can be synthesized by all known methods. It is possible for example to synthesize the phthalocyanines from a phthalonitrile and a metallic salt, or from phthalonitrile and a metal-carbonyl in a solvent having a high boiling point.

The advantages and other characteristics of the invention will be exposed more precisely in the following descriptions according to the annexed figures wherein.

Figure 1:
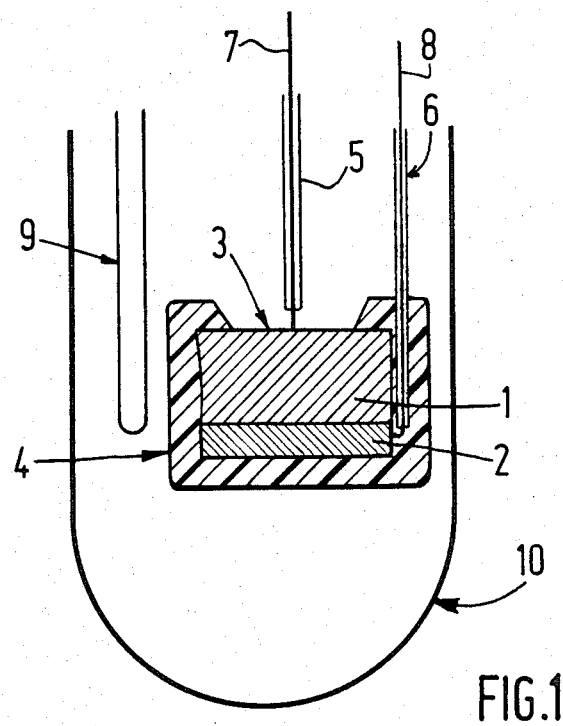
FIG. 1 represents an oxygen gauge according to the invention.

FIG. 1 represents an oxygen gauge according to the invention. It comprises essentially a solid electrolyte capsule (1), a reference electrode (2) and a working electrode (3). The reference electrode is isolated by an impervious resin (4). The electrolyte in powder form, and the reference mixture are simultaneously compressed at room temperature under a pressure of 2 tons per $cm^2$, in order to obtain a capsule comprising two layers. Platinum wires (7, 8) disposed in the alumina capillaries (5) and (6) are used as electric current mains. The temperature is measured by the platinum sensor (9), placed in proximity of the gauge. The whole device is placed in a pyrex glass tube (10) closed at the bottom and swept by a constant flux of the gas to be analyzed.

Described herein-below is the preparation of a working electrode made of iron phthalocyanine.

Iron phthalocyanine is obtained with good efficiency when prepared according to the method proposed by E. Meloni, L. Ocone and P. Block (Inorg. chem 6, 424, 1967). A solution of 8.0 g of phthalonitrile in 100 ml of 1-chloronaphthalene is heated under reflux with agitation and under nitrogen atmosphere. A solution of 3 g of $Fe(CO)_5$ in 50 ml of 1-chloronaphthalene are slowly incorporated to the above solution. The mixture thus obtained is maintained at reflux for about 30 mn after the totality of the $Fe(CO)_5$ has been added. The cooled down mixture is filtered and the undissolved product is washed with benzene, chloroform, acetone and anhydrous ether. An efficiency of 63% is thus obtained. The phthalocyanine is then purified by sublimation under a flow of nitrogen.

The phthalocyanine deposit on the solid electrolyte capsule is obtained by vacuum evaporation. The sublimation takes place in a vacuum chamber containing a support frame for the solid electrolyte capsules and a tantalum crucible containing the electrode material. The capsules are degased at least twelve hours before sublimation in order for the vacuum to reach a value of $10^{-4}$ Pa. The speed of the deposition is some Å per second. The deposited layer has a thickness of 1200 Å.

An oxygen gauge built in accordance with the invention was tested and showed the following characteristics. The electrolyte was a mixed lead fluostannate containing 0.5% of barium peroxide, the material of the reference electrode being a mixture of tin fluoride and tin in contact with the electrolyte and isolated from room temperature by a waterproof resin.

The working electrode was the same as the the one whose manufacture was described herein above, that is, iron phthalocyanine.

For test procedures, the test tube (10) with closed bottom was swept with different argon-oxygen mixtures.

Figure 2:
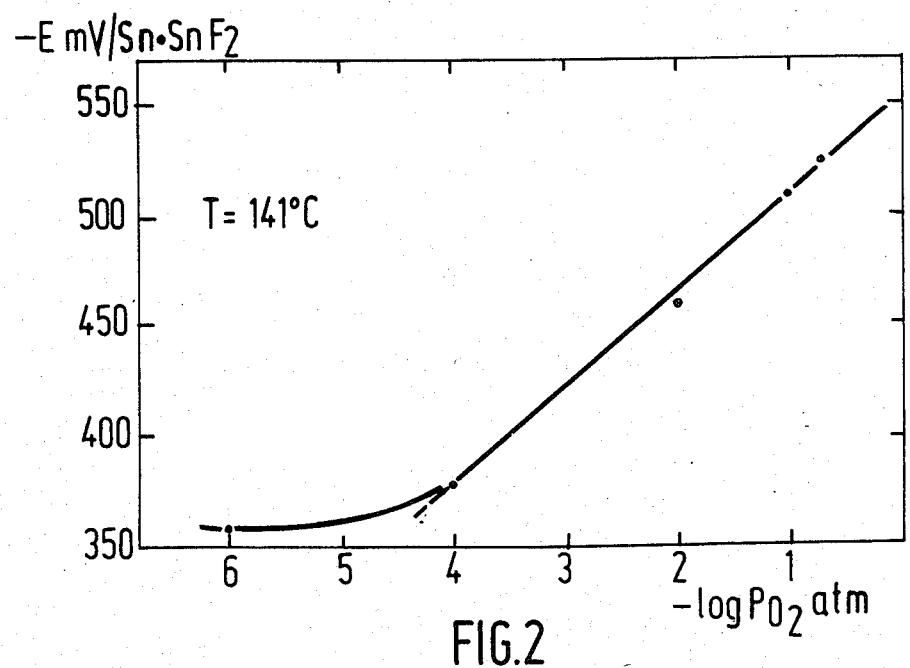
FIG. 2 represents the variation of the electromotive force of the gauge in function of the logarithm of the oxygen partial pressure at a temperature of 141° C.

In FIG. 2, the variation of the electromotive force is represented in function of the logarithm of the oxygen partial pressure, at a temperature of 141° C. It may be noted from FIG. 2 that the linear relation is well respected until $10^{-4}$ atmospheres of oxygen partial pressure, which represents a substantial improvement with respect to previously existing devices for which the linear relation was not respected for oxygen partial pressures inferior to $10^{-3}$ atmospheres. The slope of the straight line obtained corresponds to the theoretical slope, that is 41 mV/decade.

Figure 3:
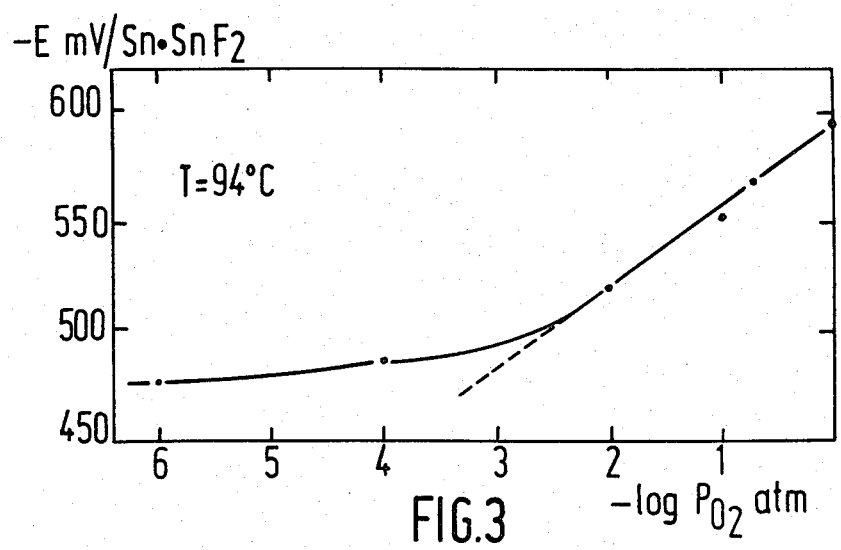
FIG. 3 represents the same variation at a temperature of 94° C.

In FIG. 3, the variation of the electromotive force of the sensor is represented in function of the logarithm of the oxygen partial pressure at a temperature of 94° C. At this function, it may be noted that the gauge responds to the partial pressure of oxygen in accordance to the theoretical law for partial pressures superior to approximtately $10^{-2}$ atmospheres. The slope of the straight line is 36 mV/decade. With conventional devices and at temperatures below 100° C. no significant variations in the electromotive force of the sensor was obtained.

Figure 4:
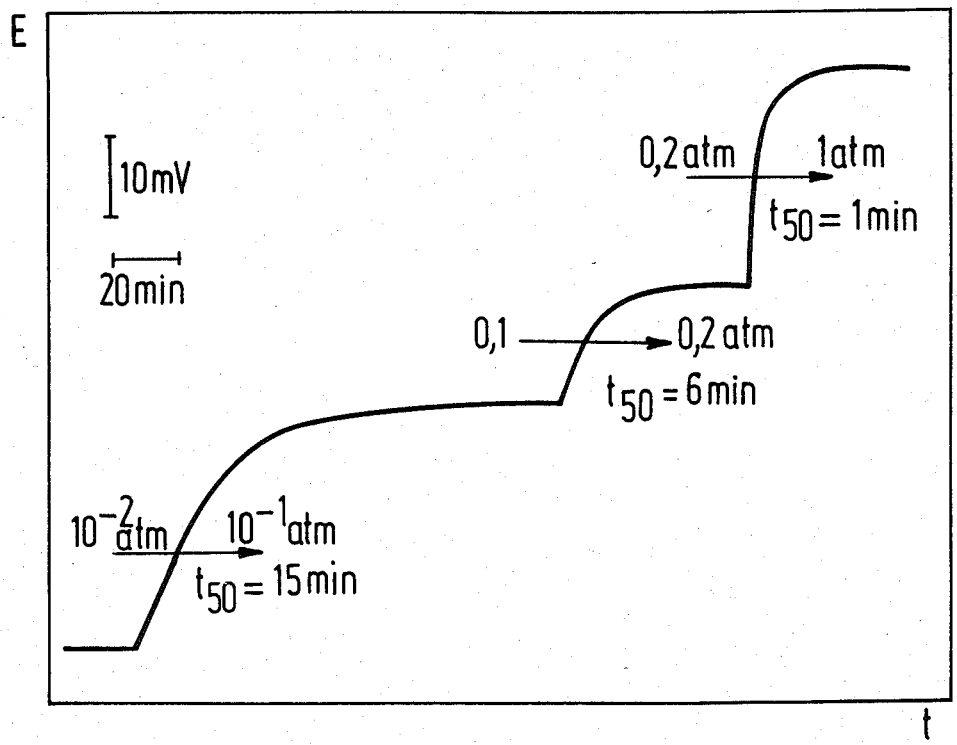
FIG. 4 represents the response time at 94° C.

Finally, in FIG. 4, the response of the sensor is represented after modification of the oxygen partial pressure and at a temperature of 94° C. The response time (t50) is 15 minutes for a modification of the pressure from $5.10^{-2}$ to $10^{-1}$ atmospheres, 1 min for a modification of 0.2 to 1 atmosphere and 6 min for a modification of 0.1 to 0.2 atmospheres.

The scope of the invention is in no way limited to the above description, in fact it encompasses all the variants as well on the level of choice of material as well as on the level of the synthesis.

We claim:

1. Electrochemical device for measuring the oxygen concentration in a gaseous medium, comprising a working electrode sensitive to oxygen, a reference electrode constituted of a gas or a solid or a mixture of solids, and a solid ion conductor electrolyte, wherein the working electrode is constituted at least in part of a macrocyclic tetrapyrolic material.

2. Electrochemical device according to claim 1, wherein the macrocyclic tetrapyrolic material is a porphyrine represented by the formula I:

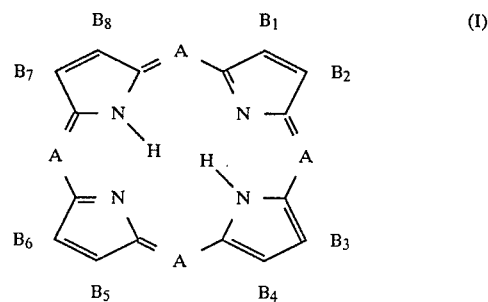

in which

A represents N or C—H or a C-phenyl group, $B_1$ to $B_8$, identical or different, each represent H or a methyl or ethyl group.

3. Electrochemical device according to claim 1, wherein the macrocyclic material is a tetra-azatetrabenzoporphyrine or a phthalocyanine represented by formula II:

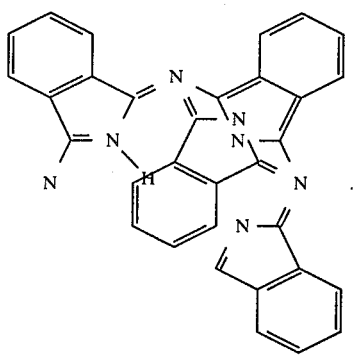

(II)

4. Electrochemical device, according to claim 3, wherein the macrocyclic material is a derivative of the compound represented by formula II obtained by substituting protons by halogen atoms consisting in chlorine or fluorine or by condensing of benzenic cycles.

5. Device according to the any one of claims 1 to 4, wherein, the macrocyclic material is in the form of a metallic complex.

6. Device according to the claim 5, wherein the metal of the complex is chosen among nickel, cobalt or iron.

* * * * *